United States Patent [19]

Pinter

[11] Patent Number: 5,872,309
[45] Date of Patent: Feb. 16, 1999

[54] METHOD FOR CHECKING THE SEALING OF A PACKAGE AND APPARATUS FOR MEASURING VISCOSITY

[75] Inventor: Stefan Pinter, Reutlingen, Germany

[73] Assignee: Robert Bosch GmbH, Stuttgart, Germany

[21] Appl. No.: 963,840

[22] Filed: Nov. 4, 1997

[30] Foreign Application Priority Data

Dec. 11, 1996 [DE] Germany ................. 196 51 384.7

[51] Int. Cl.$^6$ ................. G01N 11/00; G01P 9/00

[52] U.S. Cl. ................. 73/49.3; 73/54.01

[58] Field of Search ................. 73/52, 49.3, 54.01, 73/488; 174/52.4; 257/682

[56] References Cited

U.S. PATENT DOCUMENTS

| | | | |
|---|---|---|---|
| 5,000,047 | 3/1991 | Kato et al. | 73/706 |
| 5,187,565 | 2/1993 | Kawai et al. | 257/682 |
| 5,567,878 | 10/1996 | Kobayashi | 73/514.12 |
| 5,753,827 | 5/1998 | Cage | 73/861.356 |
| 5,788,029 | 8/1998 | Smith et al. | 188/267 |

*Primary Examiner*—Hezron Williams
*Assistant Examiner*—Jay L. Politzer
*Attorney, Agent, or Firm*—Kenyon & Kenyon

[57] ABSTRACT

A method for checking the sealing of a package, which includes a base part and a cover. A vibratory component is enclosed in a cavity in a gas of defined viscosity. Upon penetration from outside of a gas of different viscosity, the viscosity in the cavity, and thus also the vibratory properties of the vibratory element, are influenced. The sealing of the package can thus be checked at any time. The vibratory element can also be used generally to measure viscosity.

6 Claims, 1 Drawing Sheet

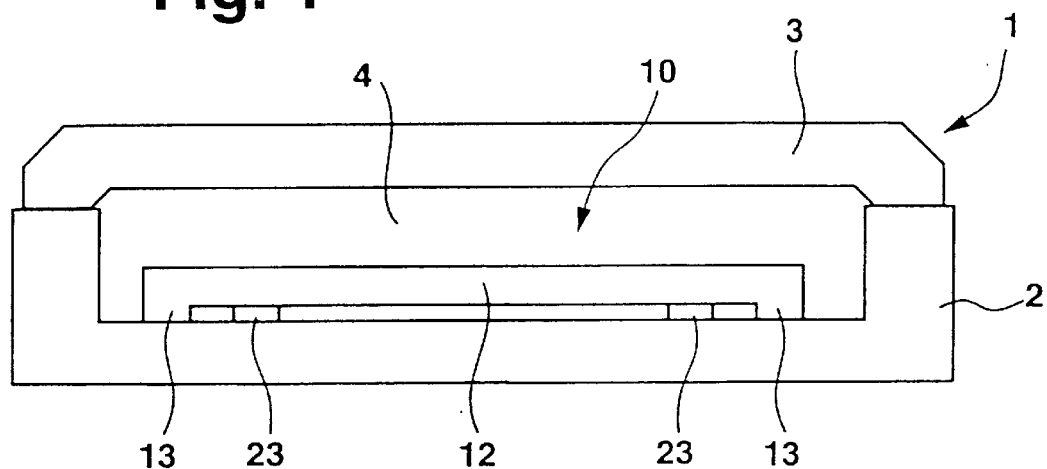
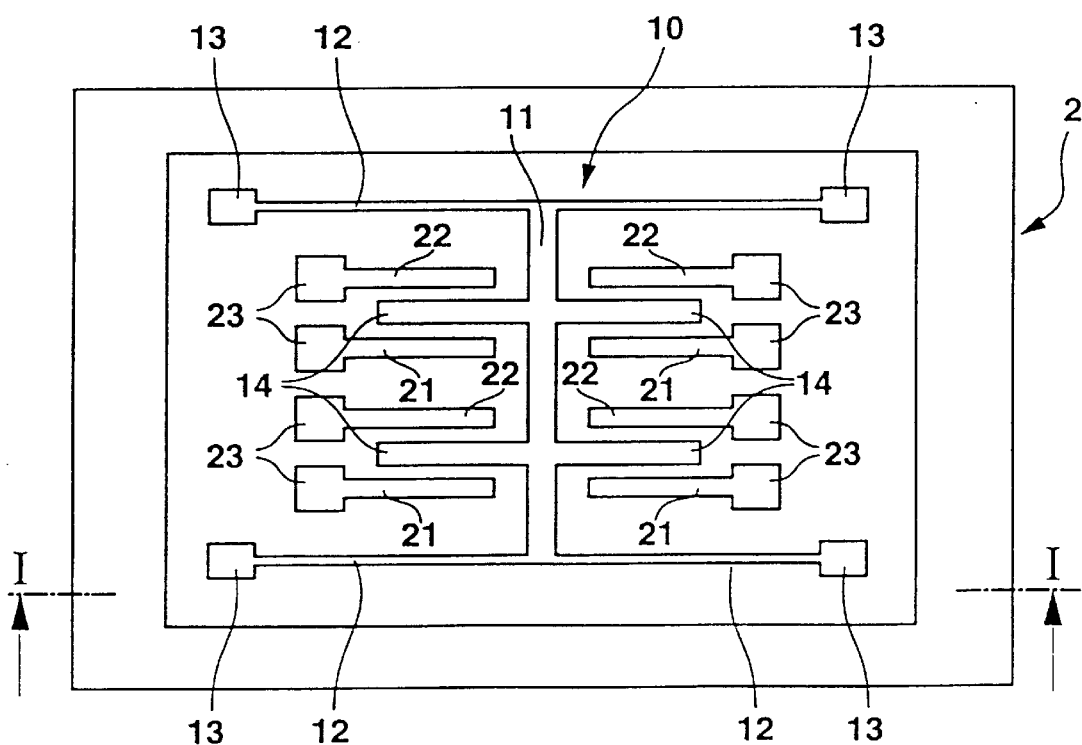

METHOD FOR CHECKING THE SEALING OF A PACKAGE AND APPARATUS FOR MEASURING VISCOSITY

BACKGROUND INFORMATION

Already known for checking the sealing of a package, in particular of a package for semiconductor components, is the "pressure cooker test," in which, in a first test phase, packaged semiconductor elements are acted upon by water at elevated pressure and temperature. In a second test phase, the semiconductor components are then investigated to determine whether they have been destroyed by the penetration of water.

SUMMARY OF THE INVENTION

The method according to the present invention has the advantage that even small impairments in the sealing of the package can be reliably detected before destruction of the contents of the package occurs. Suitable measures can thus be taken to improve the sealing of the package, or a long-term examination can be used to determine the time over which sealing of the package is sufficient.

Measurement of viscosity is accomplished in particularly simple fashion by arranging a vibratory component in the cavity; the resonance exaggeration, shift in resonant frequency, or phase can be analyzed. In order to reduce the sealing checking time, the package can be checked at elevated temperature or at elevated pressure. The method is particularly advantageous when the package is configured in the manner of the package of a vibratory micromechanical component, such as for example an acceleration sensor or a rotation rate sensor. The component being packaged can here be utilized simultaneously to check the sealing.

The apparatus according to the present invention is particularly easy to manufacture and can be used to measure a plurality of physical parameters which depend on viscosity.

BRIEF DESCRIPTION OF THE DRAWINGS

FIG. 1 shows a cross section through a package.

FIG. 2 shows a plan view of the base part of a package.

DETAILED DESCRIPTION

FIG. 1 shows a cross section through a package 1 which is constituted by a base part 2 and a cover 3. Base part 2 and cover 3 are joined to one another in such a way that a cavity 4 is formed. A vibratory component 10 is installed in cavity 4; in the cross section of FIG. 1, only anchoring elements 13, 23 and a flexural element 12 are evident. This side view of vibratory component 10 corresponds to a side view along line I—I of FIG. 2. The purpose of package 1 is to hermetically seal off cavity 4 from the environment. In particular, an enclosed gas is to remain within cavity 4, and no gases or liquids are to penetrate from outside into package 1. Vibratory element 10 can be used to check the quality of the sealing of the package. This is explained in more detail with reference to FIG. 2.

FIG. 2 shows a plan view of base part 2 of an open package 1. Vibrator 10 is arranged in the interior of the package. Vibrator 10 has a central beam 11 on which movable electrodes 14 are attached. Central beam 11 is suspended by flexural elements 4 on anchoring elements 13. Anchoring elements 13 are joined immovably to base part 2, while flexural elements 12, central beam 11, and movable electrodes 14 are not in direct contact with base part 2. These elements can, however, move relative to base part 2, in particular when forces occur which are perpendicular to the longitudinal axis of flexural elements 12. Such forces may, for example, be acceleration forces. In that case, the position of movable electrodes 14 relative to stationary electrodes 21 and 22 is modified. Stationary electrodes 21 and 22 are each joined by means of anchoring elements 23 to base plate 2, so that they cannot be moved relative to base part 2 by external forces which occur. As a result of changes in the distance between movable electrodes 14 and stationary electrodes 21 and 22, the displacement of movable electrodes 14 can be detected by measuring the capacitance between the electrodes. In addition, electrical potentials which exert a force on movable electrodes 14 can be applied to stationary electrodes 21 and 22, and at the same time, a measurement can be made of the extent to which movable electrodes 14 are moved by the forces.

The movable part of vibratory component 10, which is constituted by flexural elements 12, movable central beam 11, and movable electrodes 14, can be excited to vibrate by the application of external forces or by the application of alternating electrical voltages to stationary electrodes 21 and 22. The deflections become particularly great in this context if the frequency of the exciting vibrations matches the mechanical resonant frequency of vibratory component 10. In addition, the vibration of the vibratory component is substantially influenced by the viscosity of the gas enclosed in cavity 4. Cavity 4 can, for example, be filled with pure neon (viscosity 29.8 uPas at 0°C.; 101.3 kPa). If ordinary air, i.e. a mixture of oxygen and nitrogen, then penetrates into cavity 4 through a leak, the viscosity therefore changes (air: 17.2 uPas at 0°C.; 101.3 kPa), and so also do the vibration properties of vibratory component 10. The increased viscosity causes the damping of the vibration of vibratory element 10 to change.

This can be detected particularly easily in the presence of resonance, i.e. if the exciting force is at the mechanical resonant frequency of the vibratory system comprised of flexural elements 10, movable central beam 11, and movable electrodes 14. Even small changes in damping cause a change in the amplitude of the vibration, in the frequency at which the greatest amplitude occurs, and in the phase relationship between the exciting force and the movement of vibratory element 10 caused thereby. Sensitive conclusions as to the sealing of the package can thus be drawn on the basis of an analysis of vibration.

Since viscosity is moreover temperature-dependent, the temperature of the gas enclosed in the cavity can also be determined. Since viscosity also depends on the thermal conductivity of the enclosed gas, changes in the thermal conductivity can also be detected.

To check the package, the latter can be acted upon, at elevated temperature and at an elevated pressure, by a second gas; the second gas should have a viscosity as different as possible from that of the gas enclosed in cavity 4. Sealing can thus be checked in a relatively brief time, and predictions regarding the time profile for the penetration of external gases into cavity 4 are also possible. In addition, the sealing of the package can be checked at any time, even outside the test environment. The quality of the package can thus be checked even after a longer period of time. This is particularly interesting if the package is intended to receive electronic or micromechanical components which, for example, are to be installed in a motor vehicle and function reliably over a period of several years. A check can thus be made, for example in the context of an annual inspection, as to whether the package has become leaky because of aggressive environmental influences, so that failure of the packaged electronic or micromechanical component may thus be expected as time progresses. Such components, in particular safety-related components such as acceleration sensors for triggering restraint systems, could then be replaced in a timely fashion before they cease to function.

Vibratory component 10 shown in FIG. 2 is, for example, a sensor which is also used to measure accelerations. An acceleration sensor of this kind can thus, in accordance with the method according to the present invention, simultaneously also be used to check the sealing of the package. This applies in general to all vibratory micromechanical components, for example rotation rate sensors or vibratory membranes.

In this description, only the inclusion of a gas in cavity 4 will be described. All considerations also apply correspondingly, however, for a liquid.

The vibrator shown in FIGS. 1 and 2 can be used generally, i.e. even outside a housing, to measure viscosity. By measuring viscosity, it is thus possible to detect a plurality of magnitudes which are related to viscosity. For example, the composition of a medium including two components having different viscosities (e.g. the concentration of nitrogen in air) can be determined. The temperature can also be determined, since viscosity is temperature-dependent. In addition, the thermal conductivity of gases can be determined using the equation $$\lambda = \alpha \times \eta \times C_v$$

where $\lambda$ is the thermal conductivity; $\alpha$ is a number that is 2.4 for monatomic, 1.9 for diatomic, and 1.6 for triatomic gases; $\eta$ is the viscosity; and $C_v$ is the specific heat at constant volume.

In addition to the comb-like structure shown in FIGS. 1 and 2, other planar micromechanical structures such as beams, plates, membranes, or cylinders are also suitable as the apparatus for measuring viscosity. Planar micromechanical elements are manufactured using manufacturing methods that are known from semiconductor technology, sacrificial layers being used in order to produce movable structures.

What is claimed is:

1. A method for checking a sealing of a package for an electrical component, comprising the steps of:

enclosing at least one of a first gas or a first liquid in a cavity in an interior of the package, the at least one of the first gas or the first liquid having a first predetermined viscosity; and detecting a change in viscosity caused by at least one of a second gas or a second liquid penetrating into the cavity from an exterior of the package, the at least one of the second gas or the second liquid having a second predetermined viscosity different than the first predetermined viscosity.

2. The method according to claim 1, further comprising the step of causing a vibratory component in the cavity to vibrate, the change in viscosity being detected by a damping of vibrations of the vibratory component.

3. The method according to claim 2, wherein the damping is determined by analyzing at least one of a resonance exaggeration, a resonant frequency, and a phase of the vibratory component.

4. The method according to claim 1, wherein the package is stored at an elevated temperature in the at least one of the second gas or the second liquid.

5. The method according to claim 1, wherein the package is stored at an elevated pressure in the at least one of the second gas or the second liquid.

6. The method according to claim 2, wherein:

in a test phase, the vibratory component is used to determine the change in viscosity; and in a normal operating phase, the vibratory component is used to measure at least one of an acceleration, a rotation rate, and a pressure.

* * * * *